US006462216B1

(12) United States Patent
Fujita

(10) Patent No.: US 6,462,216 B1
(45) Date of Patent: Oct. 8, 2002

(54) PROCESS FOR PRODUCING PHOSPHOROHALIDATE

(75) Inventor: Yasunori Fujita, Kyoto (JP)

(73) Assignee: Daihachi Chemical Industry Co., Ltd., Osaka (JP)

( * ) Notice: Subject to any disclaimer, the term of this patent is extended or adjusted under 35 U.S.C. 154(b) by 0 days.

(21) Appl. No.: 09/913,144

(22) PCT Filed: Jan. 28, 2000

(86) PCT No.: PCT/JP00/00508

§ 371 (c)(1),
(2), (4) Date: Aug. 9, 2001

(87) PCT Pub. No.: WO00/49024

PCT Pub. Date: Aug. 24, 2000

(30) Foreign Application Priority Data

Feb. 16, 1999 (JP) ........................................... 11-37480

(51) Int. Cl.[7] ........................................... C07F 9/02
(52) U.S. Cl. ........................................... 558/102; 558/92
(58) Field of Search .......................... 558/87, 90, 92, 558/102

(56) References Cited

U.S. PATENT DOCUMENTS 2,938,048 A * 5/1960 Odenweller et al.
3,077,491 A * 2/1963 Seglin et al.
3,125,529 A * 3/1964 Simmons et al.
3,153,081 A * 10/1964 Markley et al.
3,189,634 A * 6/1965 Wheeler et al.
3,484,491 A * 12/1969 Ito et al.
4,948,908 A 8/1990 Frommer et al.
5,565,601 A * 10/1996 Ihara et al. ................ 558/102

FOREIGN PATENT DOCUMENTS

| | | |
|---|---|---|
| EP | 0 822 197 A2 | 2/1998 |
| GB | 651 656 | 4/1951 |
| JP | 8-198885 | 8/1996 |

* cited by examiner

*Primary Examiner*—Jean F. Vollano
(74) *Attorney, Agent, or Firm*—Knobbe, Martens, Olson and Bear, LLP

(57) ABSTRACT

The present invention provides a process for producing phosphorohalidate characterized in that a crude reaction product obtained by reacting a phosphorus oxyhalide with an aromatic hydroxy compound in the presence of a Lewis acid catalyst is purified by distillation in the presence of an alkali metal salt. The process of the invention produces a high-purity phosphorohalidate in high yield which contains no impurities such as the phosphorus oxihalidate and aromatic hydroxy compound used as starting materials and the catalyst.

17 Claims, No Drawings

PROCESS FOR PRODUCING PHOSPHOROHALIDATE

This application is the U.S. National Phase under 35 U.S.C. §371 of International Application PCT/JP00/00508, filed Jan. 28, 2000, which claims priority based on JP 1999-37480, filed Feb. 16, 1999.

TECHNICAL FIELD

The present invention relates to a process for producing phosphorohalidate (halogenated phosphoric acid ester).

BACKGROUND ART

Phosphorohalidates are chemical substances which are useful in a wide variety of fields as raw materials or intermediates for pharmaceutical preparations, agricultural chemicals and the like or as resin additives such as flame retardants, plasticizers and the like or intermediates thereof. For such uses, the purity should be as high as possible.

Phosphorohalidates are usually obtained by reacting a phosphorus oxyhalide with an aromatic hydroxy compound. A Lewis acid catalyst is often used for the purpose of suppressing the generation of the by-product triaryl phosphate during the reaction and increasing the reaction rate.

However, in such a method of producing phosphorohalidates, the crude product obtained from the reaction usually contains not only its reaction products, i.e., phosphorodihalidate and phosphoromonohalidate, but also the Lewis acid catalyst, the by-product triaryl phosphate, and the starting materials, i.e., phosphorus oxyhalide and aromatic hydroxy compound. As a result, in order to produce high purity phosphorodihalidate suitable for use as a pharmaceutical raw material or intermediate or as a reaction retarding agent for molding sand, etc., the crude phosphorohalidates obtained from the reaction (crude reaction product) need to be purified by distillation and each component contained in the crude reaction product needs to be isolated. However, when a crude reaction product containing a Lewis acid catalyst is distilled, a disproportionation reaction occurs during the distillation process. Two molecules of phosphorodihalidate tend to convert into one molecule of phosphoromonohalidate and one molecule of phosphorus oxyhalide. Two molecules of phosphoromonohalidate tend to convert into one molecule of phosphate and one molecule of phosphorodihalidate. Therefore, the purity and yield of the desired phosphorohalidate can not be substantially increased even through purification by distillation.

DISCLOSURE OF INVENTION

A primary object of the invention is to solve the above problem and provide a process for producing high-purity phosphorohalidate in a higher yield using a Lewis acid catalyst. The process can produce phosphorohalidate containing no impurities such as the phosphorus oxihalidate and aromatic hydroxy compound used as starting materials and the catalyst.

The present inventors carried out intensive research to solve the problem and found the following: when a crude reaction product obtained by reacting a phosphorus oxyhalide with an aromatic hydroxy compound in the presence of a Lewis acid catalyst is purified by distillation in the presence of an alkali metal salt, the disproportionation reaction is suppressed and the desired phosphorohalidate can be obtained in high purity and high yield by an economical and simple distillation process. The present invention was accomplished based on the above finding.

Specifically, the present invention provides the following processes for producing phosphorohalidate and for purifying the same.

1. A process for producing phosphorohalidate, the process being characterized in that a crude reaction product obtained by reacting a phosphorus oxyhalide with an aromatic hydroxy compound in the presence of a Lewis acid catalyst is purified by distillation in the presence of an alkali metal salt.
2. The process for producing phosphorohalidate according to item 1 wherein the alkali metal salt is an alkali metal carbonate.
3. The process for producing phosphorohalidate according to item 1 or 2, wherein 0.25 to 10 moles of the alkali metal salt is used per mole of the Lewis acid catalyst.
4. The process for producing phosphorohalidate according to any one of items 1 to 3, wherein the distillation for purification is carried out at a temperature of 20 to 230° C.
5. The process for producing phosphorohalidate according V to any one of items 1 to 4, wherein the phosphorohalidate is at least one member selected from the group consisting of diphenylphosphoromonochloridate and monophenylphosphorodichloridate.
6. A process for purifying phosphorohalidate, the process being characterized in that a mixture containing a phosphorodihalidate, a phosphoromonohalidate and a Lewis acid catalyst is purified by distillation in the presence of an alkali metal salt.

The process for producing phosphorohalidate according to the present invention is characterized in that the crude reaction product obtained by reacting a phosphorus oxyhalide with an aromatic hydroxy compound in the presence of a Lewis acid catalyst is purified by distillation in the presence of an alkali metal salt. In this description, this process is divided into two steps, i.e., a step for producing a crude reaction product from a phosphorus oxyhalide and an aromatic hydroxy compound (hereinafter referred to as "reaction step") and a step for purifying the crude reaction product by distillation (hereinafter referred to as "purification step"), and is described below.

Reaction Step

In the reaction step, a phosphorus oxyhalide and an aromatic hydroxy compound are reacted in the presence of a Lewis acid catalyst.

Useful phosphorus oxyhalides include, for example, phosphorus oxychloride, phosphorous oxybromide and the like. Preferred is phosphorus oxychloride. The phosphorus oxyhalides can be used singly or in combinations of two or more.

Useful aromatic hydroxy compounds include, for example, compounds having an OH group directly bound to an aromatic ring such as a benzene ring, a naphthalene ring or an anthracene ring, i.e., aromatic compounds having a phenolic OH group. In addition, one to three substituents such as alkyl groups or halogen atoms may be bound to the aromatic ring. Two or more of the aromatic rings may be bound to each other with a single bond, an alkylene group, a sulfone group, etc. Alkyl groups useful as substituents on the aromatic rings include straight or branched chain alkyl groups having about 1 to 9 carbon atoms, such as methyl, ethyl, n-propyl, isopropyl, n-butyl, sec-butyl, tert-butyl, isobutyl, hexyl, heptyl, octyl, nonyl and the like. Useful halogen atoms include chlorine, bromine and the like.

Specific examples of aromatic hydroxy compounds include phenol, (o-, m- or p-)methylphenol, (o-, m- or p-)ethylphenol, (o-, m- or p-)n-propylphenol, (o-, m- or p-)isopropylphenol, (o-, m- or p-)n-butylphenol, (o-, m- or p-)sec-butylphenol, (o-, m- or p-)tert-butylphenol, (o-, m- or p-)isobutylphenol, (o-, m- or p-)tert-butyl-2-methylphenol, (o-, m- or p-)tert-butyl-4-methylphenol, (o-, m- or p-)pentylphenol, (o-, m- or p-)hexylphenol, (o-, m- or p-)heptylphenol, (o-, m- or p-)octylphenol, (o-, m- or p-)nonylphenol, (o-, m- or p-)chlorophenol, (o-, m- or p-)bromophenol, (2,3-, 2,4-, 2,5-, 2,6-, 3,4- or 3,5-) dimethylphenol, (2,3-, 2,4-, 2,5-, 2,6-, 3,4- or 3,5-) diethylphenol, (2,3-, 2,4-, 2,5-, 2,6-, 3,4- or 3,5-)di-n-propylphenol, (2,3-, 2,4-, 2,5-, 2,6-, 3,4- or 3,5-) diisopropylphenol, (2,3-, 2,4-, 2,5-, 2,6-, 3,4- or 3,5-)di-n-butylphenol, (2,3-, 2,4-, 2,5-, 2,6-, 3,4- or 3,5-)di-sec-butylphenol, (2,3-, 2,4-, 2,5-, 2,6-, 3,4- or 3,5-)di-tert-butylphenol, (2,3-, 2,4-, 2,5-, 2,6-, 3,4- or 3,5-) dichlorophenol, (2,3-, 2,4-, 2,5-, 2,6-, 3,4- or 3,5-) dibromophenol, (2,3,5-, 2,4,5-, 2,3,6-, 2,3,4-, 2,4,6- or 3,4, 5-)trimethylphenol, (2,3,5- 2,4,5-, 2,3,6-, 2,3,4-, 2,4,6- or 3,4,5-)triethylphenol, (2,3,5-, 2,4,5-, 2,3,6-, 2,3,4-, 2,4,6- or 3,4,5-)tripropylphenol, (2,3,5-, 2,4,5-, 2,3,6-, 2,3,4-, 2,4,6- or 3,4,5-)tri-tert-butylphenol, (2,3,5-, 2,4,5-, 2,3,6-, 2,3,4-, 2,4,6- or 3,4,5-)trichlorophenol, (2,3,5-, 2,4,5-, 2,3,6-, 2,3, 4-, 2,4,6- or 3,4,5-)tribromophenol, hydroquinone, resorcin, catechol, bisphenol A, bisphenol S, bisphenol F, (1- or 2-)naphthol, (2,2'-, 4,4'-, 2,3-)biphenol, (1-, 2- or 9-)anthracenol and the like. Herein, “o-, m- or p-” means that the benzene ring has a substituent at the ortho position, metha-position or para-position. “2,3-, 2,4-, 2,5-, 3,4- or 3,5-” means that the benzene ring has substituents at the 2,3-, 2,4-, 2,5-, 3,4- or 3,5-positions. “2,3,5-, 2,4,5-, 2,3,6-, 2,3,4-, 2,4,6- or 3,4,5-” means that the benzene ring has substituents at the 2,3,5-, 2,4,5-, 2,3,6-, 2,3,4-, 2,4,6- or 3,4,5-positions. The same shall be applied hereinafter.

These aromatic hydoxy compounds may be used singly or in combinations of two or more.

Among the aromatic hydoxy compounds, phenol, methylphenol, dimethylphenol and the like are preferred from the viewpoint of commercial availability. Particularly preferred is phenol.

The reaction is preferably carried out using about 0.25 to 4 moles of the aromatic hydroxy compound per mole of the phosphorus oxyhalide. A specific mixing ratio for the reaction may be selected according to the desired phosphorohalidate. For example, a reduced phosphorus oxyhalide/hydroxy compound molar ratio produces a larger proportion of diphenylphosphoromonohalidate. An increased phosphorus oxyhalide/hydroxy compound molar ratio produces a larger proportion of phenylphosphorodihalidate.

Usable Lewis acid catalysts include known ones. Specific examples are aluminum chloride, magnesium chloride, zinc chloride, ferric chloride, stannic chloride, titanium tetrachloride and the like. Especially preferred is anhydrous magnesium chloride. The Lewis acid catalysts may be used singly or in combinations of two or more.

Preferably, the Lewis acid catalyst is used in a proportion of about 0.01 to 2 parts by weight per 100 parts by weight of the phosphorus oxyhalide, more preferably about 0.1 to 1 parts by weight. An excess of the Lewis acid catalyst tends to increase the occurrence rate of side reaction, resulting in a lower yield. On the other hand, an insufficient amount of the catalyst tends to achieve insufficient catalytic effect.

The reaction between the phosphorus oxyhalide and the aromatic hydroxy compound, i.e., the esterification reaction, can be carried out at atmospheric pressure or under reduced pressure. Generally, the reaction is preferably carried out in the absence of water. The reaction is usually carried out at 20° C. to 230° C. A preferable range is between 50° C. and 200° C. A suitable reaction temperature may be selected according to the desired phosphorohalidate.

The reaction time varies depending on the amounts and kinds of starting materials used, reaction temperature, and the like. The reaction time may be suitably chosen to selectively and efficiently produce the desired phosphorohalidate.

The reaction may be carried out in the presence of an organic solvent, depending on the characteristics and reactivity of the starting materials and the phosphorohalidate to be obtained. Useful organic solvents include any organic solvents that can dissolve the starting materials and the reaction product, have a boiling point higher than the reaction temperature and are inert to the reaction. Examples of such organic solvents are benzene, toluene, xylene, isopropyl benzene, chlorobenzene, dichlorobenzene, dichloromethane, dichloroethane, chloroform, tetrachloromethane, n-heptane, n-hexanes and the like. These solvents may be used in combinations of two or more. The amount of the organic solvent used should be approximately enough to fully dissolve the aromatic hydroxy compound. An excess of the solvent can prolong the reaction time or require a long time to recover the organic solvent after the reaction process, thus being undesirable. When a liquid starting material is used, the other starting materials may be dissolved therein and reacted.

The reaction product from the above reaction contains phosphorohalidates. Specific examples are phosphorohalidates represented by the formula (1)

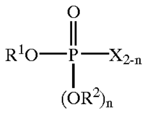

wherein $R^1$ and $R^2$ are the same or different and represent an aryl group; the aromatic ring of the aryl group may have at least one type of substituent selected from the group consisting of halogen atoms and alkyl groups; X is a halogen atom; and n is 0 or 1.

Specifically, in the formula (1), examples of the aryl groups include the same groups as the residues resulting from the removal of the OH group from the aromatic hydroxy compounds. Examples of the halogen atoms and the alkyl groups include the same as the halogen atoms and the alkyl groups which are substituents of the aromatic hydroxy compound.

Of the phosphorohalidates represented by formula (I), phosphorodihalidates wherein n=0 include, for example, phenyl phosphorodichloridate, (o-, m- or p-)chlorophenyl phosphorodichloridate, (o-, m- or p-)bromophenyl phosphorodichloridate, (o-, m- or p-)hydroxylphenyl phosphorodichloridate, (o-, m- or p-)methylphenyl phosphorodichloridate, (o-, m- or p-)ethylphenyl phosphorodichloridate, (o-, m- or p-)n-propylphenyl phosphorodichloridate, (o-, m- or p-)isopropylphenyl phosphorodichloridate, (o-, m- or p-)n-butylphenyl phosphorodichloridate, (o-, m- or p-)sec-butylphenyl phosphorodichloridate, (o-, m- or p-)tert-butylphenyl phosphorodichloridate, (o-, m- or p-)pentylphenyl phosphorodichloridate, (o-, m- or p-)hexylphenyl phosphorodichloridate, (o-, m- or p-)heptylphenyl phosphorodichloridate, (o-, m- or p-)octylphenyl phosphorodichloridate, (o-, m- or p-)nonylphenyl phosphorodichloridate, (2,3-, 2,4-, 2,5-, 2,6-, 3,4- or 3,5-) dichlorophenyl phosphorodichloridate, (2,3- 2,4-, 2,5- 2,6-, 3,4- or 3,5-) dibromophenyl phoophorodichloridate, (2,3-, 2,4-, 2,5-, 2,6-, 3,4- or 3,5-)dimethylphenyl phosphorodichloridate, (2,3-, 2,4-, 2,5-, 2, 6-, 3,4- or 3,5-)

diethylphenyl phosphorodichloridate, (2,3-, 2,4-, 2,5-, 2,6-, 3,4-, or 3,5-)di-n-propylphenyl phosphorodichloridate, (2,3-, 2,4-, 2,5-, 2,6-, 3,4- or 3,5-)diisopropylphenyl phosphorodichloridate, (2,3-, 2,4-, 2,5-, 2,6-, 3,4- or 3,5-) di-n-butylphenyl phosphorodichloridate, (2,3-, 2,4-, 2,5-, 2,6-, 3,4- or 3,5-)di-sec-butylphenyl phosphorodichloridate, (2,3-, 2,4-, 2,5-, 2,6-, 3,4- or 3,5-)di-tert-butylphenyl phosphorodichloridate, (2,3,5-, 2,4,5-, 2,3,6-, 2,3,4-, 2,4,6- or 3,4,5-)trimethylphenyl phosphorodichloridate, (2,3,5- 2,4,5-, 2,3,6-, 2,3,4-, 2,4,6- or 3,4,5-)triethylphenyl phosphorodichloridate, tris[(2,3,5-, 2,4,5-, 2,3,6-, 2,3,4-, 2,4,6- or 3,4, 5-)tripropylphenyl phosphorodichloridate and like aryl phosphorodihalidates.

Phosphoromonohalidates wherein n=1 include, for example, diphenyl phosphoromonochloridate, (o-, m- or p-)dichlorophenyl phosphoromonochloridate, (o-, m- or p-)dibromophenyl phosphoromonochloridate, (o-, m- or p-)dihydroxylphenyl phosphoromonochloridate, (o-, m- or p-)dimethylphenyl phosphoromonochloridate, (o-, m- or p-)diethylphenyl phosphoromonochloridate, (o-, m- or p-)di-n-propylphenyl phosphoromonochloridate, (o-, m- or p-)diisopropylphenyl phosphoromonochloridate, (o-, m- or p-)di-n-butylphenyl phosphoromonochloridate, (o-, m- or p-)di-sec-butylphenyl phosphoromonochloridate, (o-, m- or p-)di-tert-butylphenyl phosphoromonochloridate, (o-, m- or p-)dipentylphenyl phosphoromonochloridate, (o-, m- or p-)dihexylphenyl phosphoromonochloridate, (o-, m- or p-)diheptylphenyl phosphoromonochloridate, (o-, m- or p-)dioctylphenyl phosphoromonochloridate, (o-, m- or p-)dinonylphenyl phosphoromonochloridate, bis-(2,3-, 2,4-, 2,5-, 2,6-, 3, 4- or 3,5-)dichlorophenyl phosphoromonochloridate, bis-(2,3- 2,4-, 2,5- 2, 6-, 3,4- or 3,5-)dibromophenyl phosphoromonochloridate, bis-(2,3-, 2,4-, 2,5-, 2,6-, 3,4- or 3,5-)dimethylphenyl phosphoromonochloridate, bis-(2,3-, 2,4-, 2,5-, 2,6-, 3, 4-or 3,5-)diethylphenyl phosphoromonochloridate, bis-(2,3-, 2,4-, 2,5-, 2,6-, 3,4- or 3, 5-)di-n-propylphenyl phosphoromonochloridate, bis-(2,3-, 2,4-, 2,5-, 2,6-, 3, 4-or 3,5-)diisopropylphenyl phosphoromonochloridate, bis-(2, 3-, 2,4-, 2,5-, 2,6-, 3,4- or 3, 5-)di-n-butylphenyl phosphoromonochloridate, bis-(2,3-, 2,4-, 2,5-, 2, 6-, 3,4- or 3,5-)di-sec-butylphenyl phosphoromonochloridate, bis-(2, 3-, 2,4-, 2,5-, 2,6-, 3,4- or 3,5-)di-tert-butylphenyl phosphoromonochloridate, bis-(2,3,5-, 2,4,5-, 2,3,6-, 2,3,4-, 2,4,6- or 3,4,5-)trimethylphenyl phosphoromonochloridate, bis-(2,3,5- 2,4,5-, 2,3,6-, 2,3,4-, 2,4,6- or 3,4,5-) triethylphenyl phosphoromonochloridate, bis-(2,3,5-, 2,4,5-, 2,3,6-, 2,3,4-, 2,4,6- or 3,4,5-)tripropylphenyl phosphoromonochloridate and like diaryl phosphoromonohalidates.

The crude product thus obtained from the reaction contains a phosphorodihalidate, a phosphoromonohalidate and the catalyst residue. Under certain reaction conditions, it may also contain unreacted starting materials, triaryl phosphate and the like.

Purification Step

In the purification step, the crude reaction product obtained from the reaction step is purified by distillation in the presence of an alkali metal salt.

The means of purification by distillation can be roughly classified into batch distillations and continuous distillations. These distillations are further divided into atmospheric distillations and reduced pressure distillations. Any of these distillation means can be used in the present invention. A specific distillation means can be selected according to the composition and amount of the crude reaction product to be treated and the like. Particularly preferred are distillations under reduced pressure because the crude reaction product is subjected to a lower amount of heat, resulting in suppression of the disproportionation reaction.

Using rectification equipment is an effective way to isolate a phosphorodihalidate or a phosphoromonohalidate as a single compound from phosphorohalidates.

With regard to the conditions for purification by distillation, the degree of vacuum, distillation temperature, distillation time and the like can be selected according to the types and amounts of phosphorohalidates and catalyst in the crude reaction product, etc.

For commercial scale manufacturing, the degree of vacuum is preferably in the range of about 0.5 to 300 mmHg.

The distillation temperature is preferably in the range of about 20° C. to 230° C. A distillation temperature higher than 230° C. is undesirable because it tends to drastically accelerate the disproportionation reaction of phosphorohalidate. On the other hand, if the temperature is lower than 20° C., a large amount of energy is required to cool the distillate with the condenser, thus being undesirable.

The alkali metal salt used in the distillation system is preferably in a proportion of about 0.25 to 10 moles per mole of the Lewis acid catalyst used in the reaction process, more preferably about 0.5 to 2 moles. If the amount of the alkali metal salt used is too small, it is not possible to sufficiently suppress disproportionation. On the other hand, an excess of the alkali metal salt does not further increase its effects, thus being uneconomical. Furthermore, an excess of the metal salt has the adverse effect of tending to decompose the desired product.

Examples of alkali metal salts include carbonates such as sodium carbonate, sodium hydrogencarbonate, potassium carbonate and potassium hydrogencarbonate; and chlorides such as sodium chloride and potassium chloride. Carbonates are preferred because even a small amount of carbonate can sufficiently suppress the disproportionation of phosphorohalidates. Particularly preferred is sodium carbonate. In this case, the alkali metal salt is solid and the crude reaction product is liquid. Therefore, it is preferable that the two components be in sufficient contact with each other, particularly preferably by stirring during distillation or fully stirring before distillation. A larger contact area between the alkali metal salt and the crude reaction product results in a greater disproportionation suppression effect. Therefore, fine powder of alkali metal salt is preferable to granular one.

In the case of using a solvent in the reaction process or reacting a hydroxy compound with an excess of phosphorus oxyhalide, it is preferable that the solvent, phosphorus oxyhalide and like low boiling point compounds and hydrogen chloride contained in the crude reaction product be removed by evaporation before the distillation process.

According to the above process of purification by distillation, phosphorodihalidate and phosphoromonohalidate can be separated from the crude reaction product and obtained with high purity in high yield. Phosphorodihalidate or phosphoromonohalidate can also be isolated as a single compound in high purity and high yield.

The purification step can be carried out subsequently to the reaction step in a process for producing phosphorohalidate. Alternatively, the purification step can be carried out as a purification method for a mixture containing phosphorodihalidate, phosphoromonohalidate and Lewis acid catalyst, independently from the reaction step. For example, after repeated production of the crude reaction product by reacting a phosphorus oxyhalide with an aromatic hydroxy compound, the crude product is transferred to a treatment vessel other than the reaction vessel. The distillation treatment is then carried out under the above conditions, whereby phosphorohalidates can be separated from a mixture of phosphorodihalidate, phosphoromonohalidate and Lewis acid catalyst and obtained with high purity in high yield. Such a process efficiently provides phosphorohalidates.

Known purification methods such as filtration and membrane separation can be used to purify the phosphorohalidates obtained by the process of the present invention, provided that the purification methods do not adversely affect the product.

The qualities such as purity, hue and metal content of the phosphorohalidates obtained by the process of the invention can be controlled to match needs by appropriately selecting the production conditions in the above production process and optionally further using one or more other known purification methods.

Effects of the Invention

The production process of the present invention can suppress the disproportionation reaction more effectively than the conventional purification processes by distillation, resulting in reduction of by-products and achieving production of phosphorohalidates in high purity and high yield. This production process is especially advantageous for producing high-purity phosphorodihalidate or phosphoromonohalidate as a single compound.

BEST MODE FOR CARRYING OUT THE INVENTION

The present invention will be described below in more detail with reference to Examples.

In Examples, the content of each component was measured by gas chromatography (equipment name: "GC-14A", manufactured by Shimadzu Corporation, Conditions: sample injection volume: 0.4 $\mu$l, column length: 2.1 m, temperature rising rate: 16° C./min. (from 100° C. to 200° C.), filler: Silicone HV grease, carrier: Gaschrom Z (particle size 80–100 mesh), reference column: the same as above, carrier gas: He, flow rate: 50 ml/min-atm, detector: TCD (current 50 mA), detector temperature: 280° C., injection temperature: 280° C.). The metal content in the product was determined in accordance with JIS K0116 by ICP (Inductively Coupled Plasma Spectrometry).

The disproportionation rate was calculated according to the equation shown below and used as the measure of yield. Specifically, a lower disproportionation rate of the desired compound indicates successful suppression of disproportionation and means higher yield and higher purity.

Disproportionation rate (%)=[(Total weight of the target compound in fractions by distillation—weight of the target compound contained in the crude product)/weight of the target compound in the crude product]×100

EXAMPLE 1

A 2-liter four-necked flask equipped with a stirrer, a thermometer and a condenser was charged with 752 g of phenol, 1842 g of phosphorus oxychloride and 2 g of magnesium chloride (a catalyst). The mixture was stirred while it was heated and the reaction temperature was gradually raised to 95° C. over a period of 7 hours. Confirming that unreacted phenol was not left, the reaction was stopped. The hydrogen chloride gas produced during the reaction was introduced into a water scrubber. Then, the pressure was gradually reduced to 100 mmHg and the temperature was raised to 120° C. to collect the excess phosphorus oxychloride. The crude product obtained from the reaction (hereinafter referred to as "crude product (1)") weighed 1730.2 g. Table 1 shows the composition of crude product (1). In the table, compound (1) indicates phenylphosphorodichloridate, compound (2) diphenylphosphorochloridate, and compound (3) triphenylphosphate.

Subsequently, 861 g of crude product (1) and 1.1 g of sodium carbonate were added to a 1-liter four-necked flask equipped with a stirrer, a thermometer, a condenser and a receptor connected via an adaptor. Distillation was carried out under reduced pressure (31 mmHg). The initial fraction was collected at a distillation temperature from 120° C. to 141° C. The main fraction was collected at a distillation temperature from 141° C. to 158° C. over a period of 10 hours. The remainder was the residual fraction. Table 1 presented below shows the weights and compositions of the initial fraction, main fraction and residual fraction. The purity of the phenylphosphorodichloridate in the main fraction obtained by distillation was 99.8%.

EXAMPLE 2

Distillation was carried out under reduced pressure (31 mmHg) in the same manner as in Example 1 except that 0.55 g (half the amount used in Example 1) of sodium carbonate was used with 861 g of crude product (1) obtained in the same manner as in Example 1. The initial fraction was collected at a distillation temperature from 120° C. to 1410C. The main fraction was collected at a distillation temperature from 141° C. to 158° C. over a period of 10 hours. The remainder was the residual fraction. Table 1 presented below shows the weights and compositions of the initial fraction, main fraction and residual fraction. The purity of the phenylphosphorodichloridate in the main fraction obtained by distillation was 100%.

EXAMPLE 3

A 1-liter four-necked flask equipped with a stirrer, a thermometer and a condenser was charged with 376 g of phenol, 921 g of phosphorus oxychloride and 1 g of magnesium chloride (a catalyst). The mixture was stirred while it was heated and the reaction temperature was gradually raised to 90° C. over a period of 6.5 hours. confirming that unreacted phenol was not left, the reaction was stopped. The hydrogen chloride gas produced during the reaction was introduced into a water scrubber. Then, the pressure was gradually reduced to 100 mmHg and the temperature was raised to 120° C. to collect the excess phosphorus oxychloride. The crude product obtained from the reaction (hereinafter referred to as "crude product (2)") weighed 856.7 g. Table 1 presented below shows the composition of crude product (2).

Subsequently, distillation was carried out under reduced pressure (30 mmHg) in the same manner as in Example 1, except that 0.9 g of sodium chloride was used with 630.1 g of crude product (2). The initial fraction was collected at a distillation temperature from 120° C. to 141° C. The main fraction was collected at a distillation temperature from 141° C. to 158° C. over a period of 10 hours. The remainder was the residual fraction. Table 1 presented below shows the weights and compositions of the initial fraction, main fraction and residual fraction. The purity of the phenylphosphorodichloridate in the main fraction obtained by distillation was 99.9%.

Example 4

A 1-liter four-necked flask equipped with a stirrer, a thermometer and a condenser was charged with 376 g of phenol, 921 g of phosphorus oxychloride and 1 g of magnesium chloride (a catalyst). The mixture was stirred while it was heated and the reaction temperature was gradually raised to 95° C. over a period of 6.5 hours. Confirming that unreacted phenol was not left, the reaction was stopped. The hydrogen chloride gas produced during the reaction was introduced into a water scrubber. Then, the pressure was gradually reduced to 100 mmHg and the temperature was raised to 120° C. to collect the excess phosphorus oxychloride. The crude product obtained from the reaction (hereinafter referred to as "crude product (3)") weighed 850.3 g. Table 1 presented below shows the composition of crude product (3).

Subsequently, distillation was carried out under reduced pressure (30 mmHg) in the same manner as in Example 1, except that 1.1 g of sodium chloride was used with 631.2 g of crude product (3). The initial fraction was collected at a distillation temperature from 120° C. to 140° C. The main fraction was collected at a distillation temperature from 140° C. to 150° C. over a period of 10 hours. The remainder was the residual fraction. Table 2 presented below shows the weights and compositions of the initial fraction, main fraction and residual fraction. The purity of the phenylphosphorodichloridate in the main fraction obtained by distillation was 99.9%.

COMPARATIVE EXAMPLE 1

The reaction was carried out in the same manner as in Example 1 except that a 1-liter four-necked flask equipped with a stirrer, a thermometer and a condenser was charged with 329 g of phenol, 1074.5 g of phosphorus oxychloride and 0.9 g of magnesium chloride (a catalyst), and the mixture was stirred while it was heated and the reaction temperature was gradually raised to 105° C. over a period of 12 hours. After completion of the reaction, the excess phosphorus oxychloride was collected. The crude product obtained from the reaction (hereinafter referred to as "crude product (4)") weighed 744 g. Table 2 shows the composition of crude product (4).

Subsequently, 744.1 g of crude product (4) alone was distilled under reduced pressure (22 mmHg) in the same manner as in Example 1. The initial fraction was collected at a distillation temperature from 120° C. to 131° C. The main fraction was collected at a distillation temperature from 131° C. to 158° C. over a period of 10 hours. The remainder was the residual fraction. Table 2 presented below shows the weights and compositions of the initial fraction, main fraction and residual fraction. The purity of the phenylphosphorodichloridate in the main fraction obtained by distillation was 96.8%.

TABLE 1

| | | | Composition | | | | | | | |
|---|---|---|---|---|---|---|---|---|---|---|
| | | | Phosphorus oxychloride | | Compound (1) | | Compound (2) | | Compound (3) | |
| | | g | g | wt % | g | wt % | g | wt % | g | wt % |
| Example 1 | Crude product (1) | 861.0 | 65.4 | 7.6 | 728.4 | 84.7 | 66.2 | 7.7 | — | — |
| | Initial fraction | 83.6 | 62.4 | 74.7 | 21.2 | 25.3 | — | — | — | — |
| | Main fraction | 677.5 | — | — | 676.1 | 99.8 | 1.4 | 0.2 | — | — |
| | Residual fraction | 98.5 | — | — | 31.8 | 33.0 | 64.6 | 67.0 | — | — |
| | Fraction total | — | 62.4 | — | 729.1 | — | 66.0 | — | — | — |
| | Fraction total - Crude product (1) | — | −3.0 | — | +0.7 | — | −0.2 | — | — | — |
| | Disproportionation rate (%) | | | | | — | | | | |
| Example 2 | Crude product (1) | 861.0 | 65.4 | 7.6 | 728.4 | 84.7 | 66.2 | 7.7 | — | — |
| | Initial fraction | 81.2 | 67.7 | 83.4 | 13.5 | 16.6 | — | — | — | — |
| | Main fraction | 680.3 | — | — | 680.3 | 100.0 | — | — | — | — |
| | Residual fraction | 98.3 | — | — | 32.3 | 33.4 | 64.4 | 66.6 | — | — |
| | Fraction total | — | 67.7 | — | 726.1 | — | 64.4 | — | — | — |
| | Fraction total - Crude product (1) | — | +2.3 | — | −2.3 | — | −1.9 | — | — | — |
| | Disproportionation rate (%) | | | | | 0.3 | | | | |
| Example 3 | Crude product (2) | 630.1 | 35.0 | 5.6 | 558.0 | 88.7 | 36.3 | 5.8 | — | — |
| | Initial fraction | 52.7 | 35.9 | 68.1 | 16.8 | 31.9 | — | — | — | — |
| | Main fraction | 495.3 | 0.7 | 0.1 | 494.6 | 99.9 | — | — | — | — |
| | Residual fraction | 82.1 | — | — | 42.1 | 52.4 | 38.3 | 47.6 | — | — |
| | Fraction total | — | 36.6 | — | 553.5 | — | 38.3 | — | — | — |
| | Fraction total - Crude product (2) | — | +1.6 | — | −4.5 | — | +2.0 | — | — | — |
| | Disproportionation rate (%) | | | | | 0.8 | | | | |

Compound (1): Phenylphosphorodichloridate
Compound (2): Diphenylphosphorochloridate
Compound (3): Triphenylphosphate

TABLE 2

| | | | Composition | | | | | | | |
|---|---|---|---|---|---|---|---|---|---|---|
| | | | Phosphorus oxychloride | | Compound (1) | | Compound (2) | | Compound (3) | |
| | | g | g | wt % | g | wt % | g | wt % | g | wt % |
| Example 4 | Crude product (3) | 631.2 | 30.3 | 4.8 | 565.4 | 89.7 | 34.7 | 5.5 | — | — |
| | Initial fraction | 55.2 | 27.9 | 50.5 | 27.3 | 49.5 | — | — | — | — |
| | Main fraction | 493.9 | — | — | 493.4 | 99.9 | 0.5 | 0.1 | — | — |
| | Residual fraction | 79.3 | — | — | 40.2 | 51.9 | 37.2 | 48.1 | — | — |
| | Fraction total | — | 27.9 | — | 560.9 | — | 37.7 | — | — | — |
| | Fraction total - Crude product (3) | — | −2.4 | — | −4.5 | — | −3.0 | — | — | — |
| | Disproportionation rate (%) | | | | | 0.8 | | | | |
| Comparative example 1 | Crude product (4) | 744.1 | 34.2 | 4.6 | 669.6 | 90.1 | 39.4 | 5.3 | — | — |
| | Initial fraction | 52.5 | 37.4 | 71.3 | 15.1 | 28.7 | — | — | — | — |
| | Main fraction | 545.3 | 17.2 | 3.2 | 527.6 | 96.8 | 0.5 | 0.1 | — | — |
| | Residual fraction | 144.6 | — | — | 70.7 | 49.2 | 73.0 | 50.8 | — | — |
| | Fraction total | — | 54.6 | — | 613.4 | — | 73.5 | — | — | — |
| | Fraction total - Crude product (4) | — | +20.4 | — | −56.2 | — | +34.1 | — | — | — |
| | Disproportionation rate (%) | | | | | 8.4 | | | | |

Compound (1): Phenylphosphorodichloridate
Compound (2): Diphenylphosphorochloridate
Compound (3): Triphenylphosphate

Example 5

A 2-liter four-necked flask equipped with a stirrer, a thermometer and a condenser was charged with 1018 g of phenol, 884 g of phosphorus oxychloride and 1.6 g of magnesium chloride (a catalyst). The mixture was stirred while it was heated and the reaction temperature was gradually raised to 125° C. over a period of 11 hours. Confirming that unreacted phenol and phosphorus oxyhalide were not left, the reaction was stopped. The hydrogen chloride gas produced during the reaction was introduced into a water scrubber. Then, the residual hydrogen chloride was removed under reduced pressure (50 mmHg). The crude product obtained from the reaction (hereinafter referred to as "crude product (5)") weighed 1500 g. Table 3 shows the composition of crude product (5).

Subsequently, 745 g of crude product (5) and 0.9 g of sodium carbonate were added to a 1-liter four-necked flask equipped with a stirrer, a thermometer, a condenser and a receptor connected via an adaptor. Distillation was carried out under reduced pressure (5 mmHg). The initial fraction was collected at a distillation temperature from 125° C. to 180° C. The main fraction was collected at a distillation temperature from 180° C. to 191° C. over a period of 10 hours. The remainder was the residual fraction. Table 3 presented below shows the weights and compositions of the initial fraction, main fraction and residual fraction. The purity of the diphenylphosphorochloridate in the main fraction obtained by distillation was 98%.

COMPARATIVE EXAMPLE 2

745 g of crude product (5) alone was distilled under reduced pressure (7 mmHg) in the same manner as in Example 5 . The initial fraction was collected at a distillation temperature from 125° C. to 185° C. The main fraction was collected at a distillation temperature from 185° C. to 198° C. over a period of 10 hours. The remainder was the residual fraction. The purity of the diphenylphosphorochloridate in the main fraction obtained by distillation was 91%.

The metal contents of the products obtained in Examples 1–5 and comparative Examples 1 and 2 were below the detection limit (0.1 ppm).

TABLE 2

| | | | Composition | | | | | | | |
|---|---|---|---|---|---|---|---|---|---|---|
| | | | Phosphorus oxychloride | | Compound (1) | | Compound (2) | | Compound (3) | |
| | | g | g | wt % | g | wt % | g | wt % | g | wt % |
| Example 5 | Crude product (5) | 745.0 | — | — | 92.3 | 12.4 | 592.4 | 79.6 | 59.5 | 8.0 |
| | Initial fraction | 149.5 | | | 89.3 | 59.7 | 59.9 | 40.1 | 0.3 | 0.2 |
| | Main fraction | 449.5 | | — | 3.6 | 0.8 | 440.5 | 98.0 | 5.4 | 1.2 |
| | Residual fraction | 145.6 | | — | | | 88.4 | 61.4 | 55.5 | 38.6 |
| | Fraction total | — | | — | 92.9 | | 588.8 | — | 61.2 | — |
| | Fraction total - Crude product (5) | — | | — | +0.6 | — | −3.6 | — | +1.7 | — |
| | Disproportionation rate (%) | | | | | 0.6 | | | | |

TABLE 2-continued

| | | | Composition | | | | | | | |
|---|---|---|---|---|---|---|---|---|---|---|
| | | | Phosphorus oxychloride | | Compound (1) | | Compound (2) | | Compound (3) | |
| | | g | g | wt % | g | wt % | g | wt % | g | wt % |
| Comparative example 2 | Crude product (5) | 745.0 | | | 92.3 | 12.4 | 592.4 | 79.6 | 59.5 | 8.0 |
| | Initial fraction | 131.5 | | | 90.3 | 68.7 | 40.9 | 31.1 | 0.3 | 0.2 |
| | Main fraction | 462.2 | | | 36.1 | 7.8 | 420.7 | 91.0 | 5.4 | 1.2 |
| | Residual fraction | 150.2 | | — | | | 42.6 | 28.5 | 106.8 | 71.5 |
| | Fraction total | — | | — | 126.4 | — | 504.2 | — | 112.5 | — |
| | Fraction total - Crude product (5) | — | | — | +34.1 | — | −88.2 | — | +53.0 | — |
| | Disproportionation rate (%) | | | | | 14.9 | | | | |

Compound (1): Phenylphosphorodichloridate
Compound (2): Diphenylphosphorochloridate
Compound (3): Triphenylphosphate As is clear from Tables 1–3, when the desired product was phenylphosphorodichloridate (compound (1)), disproportionation did not occur in Example 1 in which distillation was carried out in the presence of sodium carbonate; in Examples 2–4 also, the disproportionation rates were extremely low and no substantial disproportionation occurred. In contrast, Comparative Example 1 in which sodium carbonate was not present had a higher disproportionation rate than the Examples, which indicates accelerated disproportionation. Similarly, when the desired product was diphenylphosphorochloridate (compound (2)), a higher disproportionation rate was found in Comparative Example 2 than in Example 5.

These results show that the process of the present invention can almost completely suppress the disproportionation of the products during purification by distillation.

I claim:

1. A process for producing phosphorohalidate, the process being characterized in that a crude reaction product obtained by reacting a phosphorus oxyhalide with an aromatic hydroxy compound in the presence of a Lewis acid catalyst is purified by distillation in the presence of at least one alkali metal salt selected from the group consisting of alkali metal carbonates, alkali metal hydrogen carbonates and alkali metal chlorides.

2. The process for producing phosphorohalidate according to claim 1 wherein the alkali metal salt is an alkali metal carbonate.

3. The process for producing phosphorohalidate according to claim 1, wherein 0.25 to 10 moles of the alkali metal salt is used per mole of the Lewis acid catalyst.

4. The process for producing phosphorohalidate according to claim 1, wherein the distillation for purification is carried out at a temperature of 20° C. to 230° C.

5. The process for producing phosphorohalidate according to claim 1, wherein the phosphorohalidate is at least one member selected from the group consisting of diphenylphosphoromonochloridate and monophenylphosphorodichloridate.

6. A process for purifying phosphorohalidate, the process being characterizedin that a mixture containing a phosphorodihalidate, a phosphoromonohalidate and a Lewis acid catalyst is purified by distillation in the presence of at least one alkali metal salt selected from the group consisting of alkali metal carbonates, alkali metal hydrogen carbonates and alkali metal chlorides.

7. The process for producing phosphorohalidate according to claim 2, wherein 0.25 to 10 moles of the alkali metal salt is used per mole of the Lewis acid catalyst.

8. The process for producing phosphorohalidate according to claim 2, wherein the distillation for purification is carried out at a temperature of 20° C. to 230° C.

9. The process for producing phosphorohalidate according to claim 3, wherein the distillation for purification is carried out at a temperature of 20° C. to 230° C.

10. The process for producing phosphorohalidate according to claim 7, wherein the distillation for purification is carried out at a temperature of 20° C. to 230° C.

11. The process for producing phosphorohalidate according to claim 2, wherein the phosphorohalidate is at least one member selected from the group consisting of diphenylphosphoromonochloridate and monophenylphosphorodichloridate.

12. The process for producing phosphorohalidate according to claim 3, wherein the phosphorohalidate is at least one member selected from the group consisting of diphenylphosphoromonochloridate and monophenylphosphorodichloridate.

13. The process for producing phosphorohalidate according to claim 4, wherein the phosphorohalidate is at least one member selected from the group consisting of diphenylphosphoromonochloridate and monophenylphosphorodichloridate.

14. The process for producing phosphorohalidate according to claim 7, wherein the phosphorohalidate is at least one member selected from the group consisting of diphenylphosphoromonochloridate and monophenylphosphorodichloridate.

15. The process for producing phosphorohalidate according to claim 8, wherein the phosphorohalidate is at least one member selected from the group consisting of diphenylphosphoromonochloridate and monophenylphosphorodichloridate.

16. The process for producing phosphorohalidate according to claim 9, wherein the phosphorohalidate is at least one member selected from the group consisting of diphenylphosphoromonochloridate and monophenylphosphorodichloridate.

17. The process for producing phosphorohalidate according to claim 10, wherein the phosphorohalidate is at least one member selected from the group consisting of diphenylphosphoromonochloridate and monophenylphosphorodichloridate.

* * * * *

UNITED STATES PATENT AND TRADEMARK OFFICE

CERTIFICATE OF CORRECTION

PATENT NO. : 6,462,216 B1
DATED : October 8, 2002
INVENTOR(S) : Yasunori Fujita

It is certified that error appears in the above-identified patent and that said Letters Patent is hereby corrected as shown below:

Title page,
Item [86], Filing Date should read -- August 8, 2001 --

Signed and Sealed this

First Day of April, 2003

JAMES E. ROGAN
*Director of the United States Patent and Trademark Office*